United States Patent
Salnik et al.

(10) Patent No.: US 8,120,776 B1
(45) Date of Patent: Feb. 21, 2012

(54) MEASURING CHARACTERISTICS OF ULTRA-SHALLOW JUNCTIONS

(75) Inventors: Alex Salnik, San Jose, CA (US); Lena Nicolaides, Castro Valley, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 294 days.

(21) Appl. No.: 12/545,015

(22) Filed: Aug. 20, 2009

(51) Int. Cl.
*G01N 21/55* (2006.01)

(52) U.S. Cl. ........................... 356/445; 356/447

(58) Field of Classification Search .......... 356/445–448, 356/237.1–237.5
See application file for complete search history.

(56) References Cited

U.S. PATENT DOCUMENTS

| | | | |
|---|---|---|---|
| 6,989,899 B2 | 1/2006 | Salnik et al. | |
| 7,248,367 B2 | 7/2007 | Salnik et al. | |
| 7,403,022 B2 | 7/2008 | Salnik et al. | |
| 7,751,035 B2 * | 7/2010 | Clarysse et al. | 356/237.1 |

OTHER PUBLICATIONS

A. Salnik et al., "Simultaneous determination of ultra-shallow junction depth and abruptness using thermal wave technique", Rev. Sci. Instrum., 75(6), 2144 (2004).

T. Clarysse et al., "Towards nondestructive carrier depth profiling", J. Vac. Sci. Technol. B 24(3), 1139 (2006).

J. Bogdanowicz et al.,"Advances in optical carrier depth profiling through high-frequency modulated optical reflectance", J. Vac. Sci. Technol. B 26(1), 310 (2008).

* cited by examiner

*Primary Examiner* — Michael P Stafira
(74) *Attorney, Agent, or Firm* — Luedeka, Neely & Graham, P.C.

(57) ABSTRACT

Carrier activation and end-of-range defect density of ultra-shallow junctions in integrated circuits are determined using modulated optical reflectance signals, DC reflectances of pump or probe laser beams, and in-phase and quadrature signal processing. A method for determining characteristics of an ultra-shallow junction includes periodically exciting a region of the substrate using a pump laser beam, and reflecting a probe laser beam from the excited region. A modulated optical reflectance signal is measured along with DC reflectance of the probe laser beam. The modulated optical reflectance signal and DC reflectance are compared with reference signals generated from calibration substrates to determine carrier activation and end-of-range defect density in the junction.

14 Claims, 6 Drawing Sheets

MEASURING CHARACTERISTICS OF ULTRA-SHALLOW JUNCTIONS

FIELD

The current invention relates to metrology of integrated circuit substrates. More particularly, the current invention relates to measuring carrier activation and the end-of-range defect concentration in ultra-shallow integrated circuit junctions using modulated optical reflectance technology.

BACKGROUND

As integrated circuit geometries continue to shrink, manufacturers have increasingly turned to optical techniques to perform non-destructive inspection and analysis of the integrated circuits. The basis for these techniques is the idea that a substrate can be examined by analyzing the reflected energy that results when an optical beam is directed at the substrate. This type of inspection and analysis is known as optical metrology and is performed using a range of different optical techniques.

Metrology systems that use external means to induce thermal or plasma waves in a substrate under study are generally referred to as modulated optical reflectance systems. Modulated optical reflectance metrology systems are used to study a range of attributes, including material composition and layer thickness. Modulated optical reflectance systems and their associated uses are described in U.S. Pat. Nos. 4,634,290, 4,646,088, 4,679,946, 4,854,710, 5,854,719, 5,978,074, 5,074,699 and 6,452,685, the entire disclosures of which are incorporated herein by reference.

Another important use of modulated optical reflectance systems is measurement and analysis of the dopants added to integrated circuit substrates before and after their activation. Dopants are ions that are implanted into substrates, such as semiconducting substrates, such as during ion implantation. The duration of the ion implantation process is one of the factors that control the resulting dopant concentration. Generally, the ion energy used during the implantation process controls the depth of implant. Both ion concentration and depth are critical factors that determine the characteristics of the ion implantation process.

The ion implantation process damages the crystal lattice of the substrate as it receives the implanted ions. This damage is typically proportional to the concentration and depth of ions within the crystal lattice. This makes measurement of the damage an effective surrogate for direct measurement of dopant concentration and depth. Modulated optical reflectance systems are typically used to measure substrates at the completion of the ion implantation process to determine the extent of the damage. The modulated optical reflectance signal, which is proportional to the extent of the damage in the substrate, is then correlated to the implantation dose and other parameters of interest.

Dopant activation after the ion implantation step is typically performed by rapidly heating and cooling the substrate in a special chamber, or by scanning a localized heat spot from a laser beam across the surface of the substrate. This process is also known as annealing. During the annealing process, dopant ions may diffuse away from the positions that they had in the lattice after ion implantation, and form a concentration profile within the substrate (diffusion anneal). Alternately, the anneal dopant ions might stay within the same area where they were located after implant (diffusion-less anneal). The transition between the implanted region containing activated dopants and the non-implanted substrate is commonly referred to as a junction.

For advanced semiconductor manufacturing, it is generally desirable for the implanted and activated region to be shallow, typically no more than about five hundred angstroms, which depth is defined herein as an ultra-shallow junction. This is usually achieved by using a fast, diffusion-less anneal, such as a laser or spike anneal with dwell times (time at temperature) of less than a few milliseconds. While creating good carrier activation, defined as the ratio of activated ions to the total concentration of ions in the ultra-shallow junction, this type of annealing leaves certain defects at the bottom of the annealed junction. These defects are generally referred to as end-of-range damage. Depending on the implantation concentration and depth, end-of-range damage may negatively affect ultra-shallow junction quality and create junction leakage, including increased probability that the carriers will move out of the junction and into other portions the substrate. To adequately evaluate junction quality, it is important to characterize both carrier activation level and the end-of-range damage concentration in the ultra-shallow junction.

A number of techniques have been developed to characterize the effectiveness of the ultra-shallow junction process. Destructive and contact methods include secondary ion mass spectroscopy, transmission electron microscopy, spreading resistance depth profiling, and sheet resistance ($R_s$ or 4-point probe) technologies. Transmission electron microscopy has been the only technique used to evaluate end-of-range defect density. Although such techniques are capable of providing ultra-shallow junction profile information, it is at the expense of turn-around times, usually measured in days or even weeks, or at the expense of damaging the surface with contacts or breaking the substrate.

What is needed, therefore, is a reliable, non-contact, and non-destructive technique to monitor both carrier activation and end-of-range defect concentration in ultra-shallow junctions.

SUMMARY

The above and other needs are met by a method for determining characteristics of a junction formed in a substrate. In a preferred embodiment, the method includes the steps of (a) periodically exciting a region of the substrate including the junction using a pump laser beam, (b) reflecting a probe laser beam from the region of the substrate being periodically excited, (c) generating both a reflectance signal and a modulated optical reflectance signal based on the probe and pump laser beams reflected from the region of the substrate being periodically excited, and (d) comparing the reflectance signal and the modulated optical reflectance signal with reference signals to determine carrier activation and an end-of-range defect density in the junction formed in the substrate.

The reference signals may be reflectance and modulated optical reflectance signals obtained from calibration substrates that have been analyzed to determine carrier activation and the end-of-range defect density in junctions formed in the calibration substrates. The calibration substrates in some embodiments are produced using various anneal temperatures and anneal times. In some embodiments, the carrier activation and the end-of-range defect density are determined based on a relationship between measured thermal wave signal level and the anneal temperature to which the substrate was exposed during an anneal process.

Some embodiments of the method include analyzing the modulated reflected probe laser beam with a coherent demodulator to generate an in-phase component and a quadrature component of the modulated optical reflectance signal. These in-phase and quadrature components are compared with the reference signals to determine the end-of-range defect density in the junction. The end-of-range defect density may be determined based on a relationship between the in-phase and quadrature components and an anneal time during which the substrate was exposed to an anneal temperature.

The steps (a) through (d) listed above may be performed on substrates annealed at various anneal temperatures and various anneal times. Based on the modulated optical reflectance measurements made on these substrates, a plot may be generated in a coordinate system of anneal temperature versus anneal time. The plot includes a curve indicating a threshold. Data points above the curve indicate removal of substantially all end-of-range defects, and data points below the curve indicate remaining end-of-range defects. Such a plot may be used to optimize the anneal process in manufacturing.

In another embodiment, the method includes the steps of (a) periodically exciting a region of the substrate including the junction using a pump laser beam, (b) reflecting a probe laser beam from the region of the substrate being periodically excited, (c) generating a modulated optical reflectance signal based on the probe laser beam reflected from the region of the substrate being periodically excited, and (d) comparing the modulated optical reflectance signal with reference signals to determine carrier activation in the junction formed in the substrate.

In some embodiments, carrier activation is determined based on a relationship between measured modulated optical reflectance signal level, anneal temperature to which the substrate was exposed during an anneal process, and anneal time during which the substrate was exposed to the anneal temperature.

In yet another embodiment, the method includes the steps of (a) periodically exciting a region of the substrate including the junction using a pump laser beam, (b) reflecting a probe laser beam from the region of the substrate being periodically excited, (c) generating a DC reflectance signal based on the probe laser beam or the pump laser beam reflected from the region of the substrate being periodically excited, and (d) comparing the DC reflectance signal with reference signals to determine carrier activation in the junction formed in the substrate.

The reference signals can be sheet resistance signals obtained from calibration substrates produced using various anneal temperatures which have been measured to determine carrier activation.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
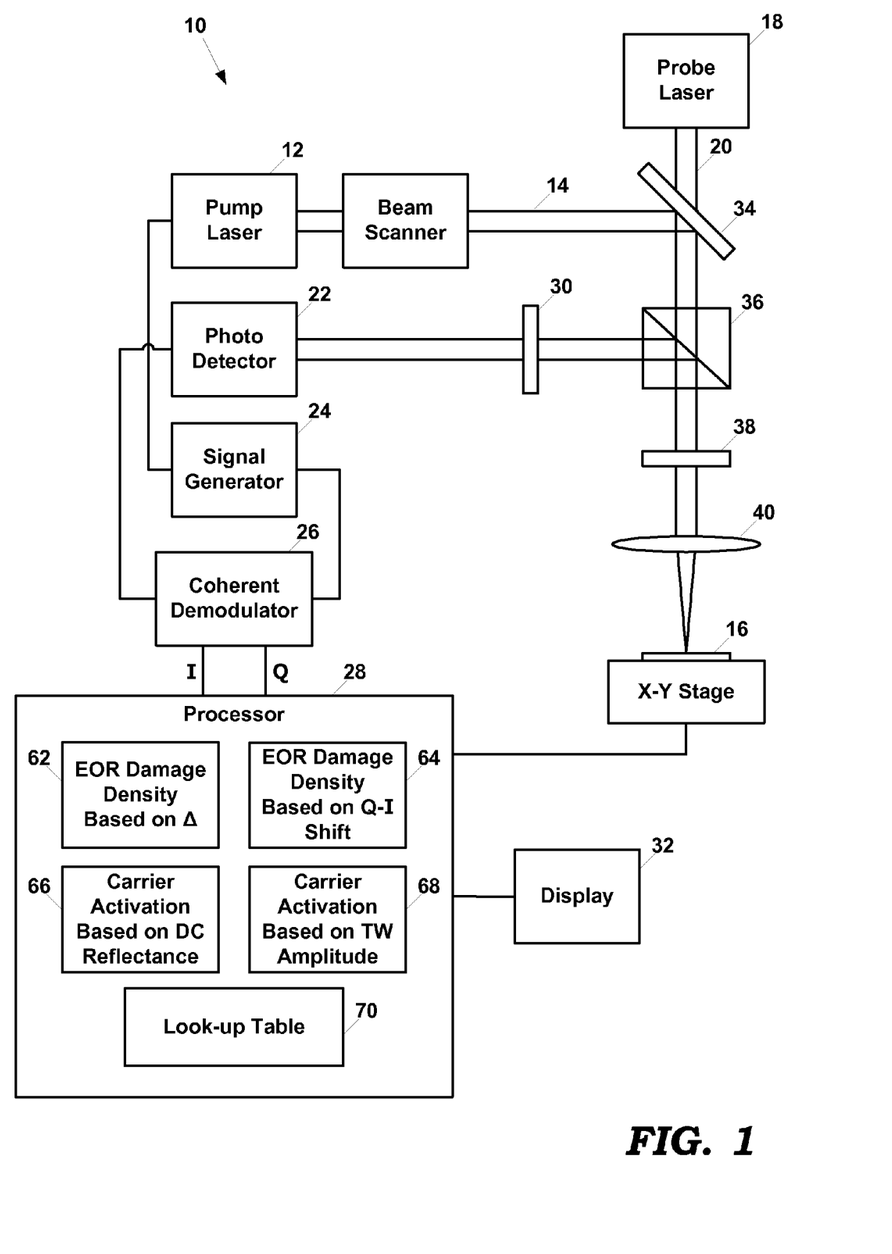
FIG. 1 depicts a functional block diagram of a modulated optical reflectance substrate metrology system according to an embodiment of the present invention.

As shown in FIG. 1, one embodiment of a modulated optical reflectance substrate measurement system 10 includes a pump laser 12 that is switched on and off to create an intensity-modulated pump beam 14. The pump beam 14 is projected against the surface of a substrate 16, causing localized periodic excitation of the substrate 16, such as a semiconducting substrate in which integrated circuits are at least partially formed. As the pump laser 12 is modulated by a signal generator 24, the localized periodic excitation creates a series of thermal and carrier plasma waves within the substrate 16. These waves reflect and scatter off various features and interact with various regions within the substrate 16 in a way that alters the flow of heat and carrier plasma from the spot on which the pump beam 14 impinges upon the substrate 16.

The presence of the thermal and carrier plasma waves has a direct effect on the surface reflectivity of the substrate 16. Features and regions below the substrate 16 surface that alter the passage of the thermal and carrier plasma waves will therefore alter the optical reflective patterns at the surface of the substrate 16. By monitoring the changes in reflectivity of the substrate 16 at the surface, information about characteristics below the surface can be investigated.

To monitor the surface changes, a probe laser 18 generates a probe beam 20 directed at a portion of the substrate 16 illuminated by the pump laser 12. The reflected probe beam 20 is directed through a filter 30 that removes the pump beam light, and a photodetector 22 records the intensity of the reflected probe beam 20. The output signal from the photodetector 22 is heterodyned with a reference signal from the signal generator 24 to isolate the changes that are synchronous with the pump beam 14 modulation. In some embodiments, this is performed using a coherent demodulator 26, which in some embodiments comprises a lock-in detector such as described in U.S. Pat. No. 5,978,074. Devices of this type typically generate separate in-phase and quadrature outputs (labeled I and Q in FIG. 1). These in-phase and quadrature outputs are provided to a processor 28 that determines the amplitude and phase of the modulated signal, and determines various physical characteristics of the substrate 16 as described in more detail hereinafter.

As shown in FIG. 1, one embodiment of the system 10 includes various optical components in the path of the probe beam 20, including an edge filter 34, a polarizing beam splitter 36, a quarter-wavelength plate 38 and a focusing lens 40.

The processor 28 uses the amplitude and phase of the modulated optical reflectance signal to determine physical characteristics of the substrate 16. In some embodiments, this is done by measuring amplitude values for one or more specially prepared calibration substrates 16, each of which has known physical characteristics. The empirically derived values are used to associate known physical characteristics with corresponding amplitude values. Amplitude values obtained for unknown substrates 16 can then be analyzed by comparison to the amplitude values obtained for the calibration substrates 16.

Figure 2A:
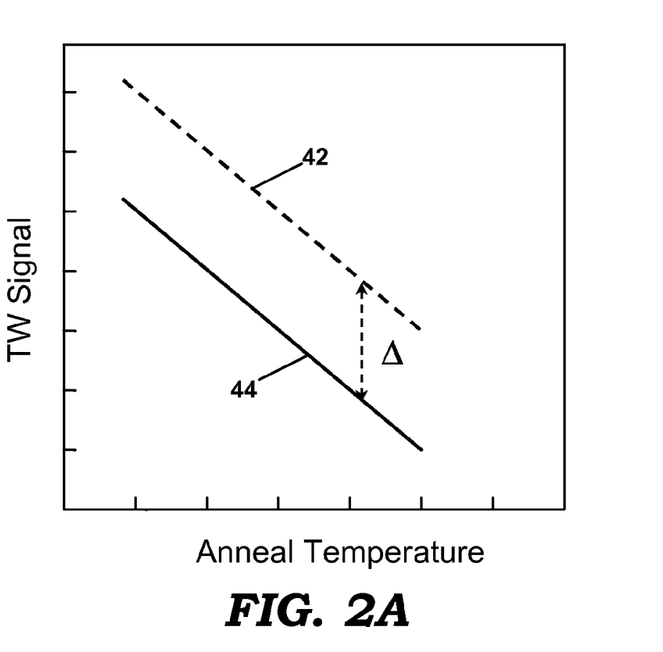
FIG. 2A depicts a plot of modulated optical reflectance signal amplitude versus anneal temperature for two anneal times according to an embodiment of the present invention.

Various embodiments of the invention use the relationship shown in FIG. 2A to determine characteristics of ultra-shallow junction structures. In this figure, the amplitude of the modulated optical reflectance signal (labeled as TW in the figures) is plotted as function of anneal temperature for two different values of anneal dwell time. Line 42 corresponds to anneal time T1 and line 44 corresponds to anneal time T2, which is greater than T1. In each case, the modulated optical reflectance signal monotonically decreases with increasing anneal temperature for a given anneal time. This is due to the fact that an increase in anneal temperature enhances carrier activation, and modifies the thermal and carrier plasma components of the modulated optical reflectance signal. The total modulated optical reflectance signal amplitude is decreasing because carrier plasma and thermal components are opposite in phase, and an increase in the plasma component leads to subtraction of an increasingly larger portion of the modulated optical reflectance signal. For the anneal time T2, the modulated optical reflectance signal dependence on anneal temperature follows the line 44, which is offset below the line 42 for time T1. A difference $\Delta$ in modulated optical reflectance signal levels caused by an increase in anneal time from time T1 to time T2 is indicative of the end-of-range defect density in the junction. Therefore, using proper calibrations to the reference substrates 16, the end-of-range defect density (which is proportional to $\Delta$) can be extracted from the dependency of the modulated optical reflectance signal on anneal temperature.

For example, a set of special reference substrates with known carrier activation levels and end-of-range damage levels is prepared by ion implantation and spike (fast) anneal. Resistivity measurements are performed on the reference substrates 16 to determine the carrier activation levels, and transmission electron microscopy analysis is performed to determine the end-of-range damage density in the reference substrates 16. Modulated optical reflectance signals are measured on the reference substrates, and the measured modulated optical reflectance levels are stored in a look-up table 70 (FIG. 1), which correlates the modulated optical reflectance signal levels to the end-of-range damage density over a predetermined range of carrier activation values corresponding to the selected anneal process. The modulated optical reflectance signal is then measured on a test substrate 16, and the end-of-range damage density of the test substrate 16 is determined by correlation of the measured modulated optical reflectance signal of the test substrate to the modulated optical reflectance signal values of the reference substrates 16 stored in the look-up table 70.

As depicted in FIG. 1, some embodiments of the invention include a software module 62 which, when executed by the processor 28, determines the end-of-range defect density based on the modulated optical reflectance signal and the reference calibration values stored in the look-up table 70.

Alternately, theoretical modeling is performed to obtain the end-of-range damage density corresponding to each implant condition (species, dose, energy, etc.) and correlation dependencies connecting the modulated optical reflectance signal and the end-of-range damage density are established. For example, this modeling is performed with software that is currently available on the Internet at http://www.srim.org/. The modulated optical reflectance signal measured on the test substrate 16 is then directly converted to the end-of-range damage density using the previously established correlation.

Figure 2B:
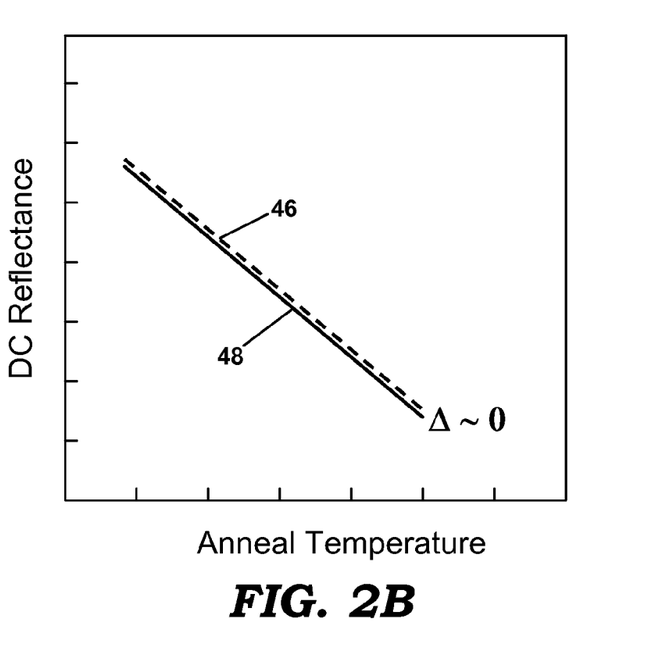
FIG. 2B depicts a plot of DC reflectance versus anneal temperature for two anneal times according to an embodiment of the present invention.
Figure 2C:
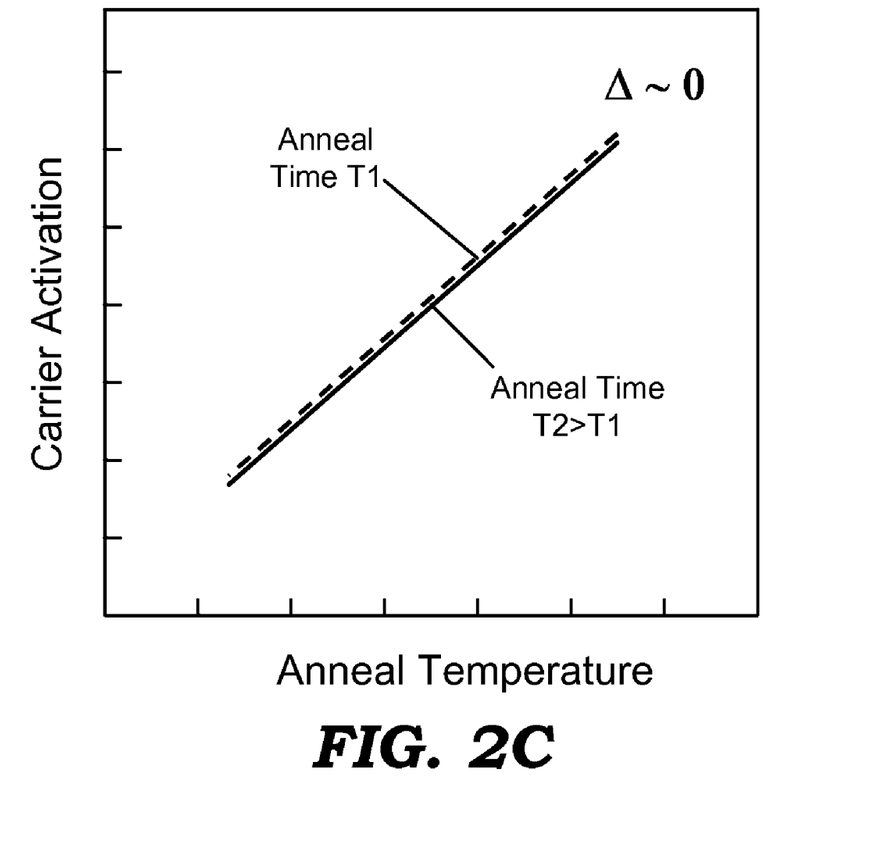
FIG. 2C depicts a plot of carrier activation versus anneal temperature for two anneal times according to an embodiment of the present invention.

Some embodiments of the invention provide several independent channels of information, including DC optical reflectances for the probe laser beam 20 and pump laser beam 14. Along with the modulated optical reflectance signal amplitude, these DC reflectances are used to characterize the ultra-shallow junction parameters. As shown in FIG. 2B, DC reflectance exhibits monotonic dependence on anneal temperature at different anneal times for the same set of substrates 16 shown in FIG. 2A, where line 46 corresponds to anneal time T1 and line 48 corresponds to anneal time T2. However, low sensitivity to end-of-range damage is observed in this case, where $\Delta$ is approximately zero. Therefore, the two channels of information, modulated optical reflectance signal and DC reflectance, in the system 10 are sensitive to different parameters of the ultra-shallow junction. The modulated optical reflectance signal is sensitive to both carrier activation and end-of-range damage density, while DC reflectance is sensitive primarily to carrier activation in the junction.

Figure 4:
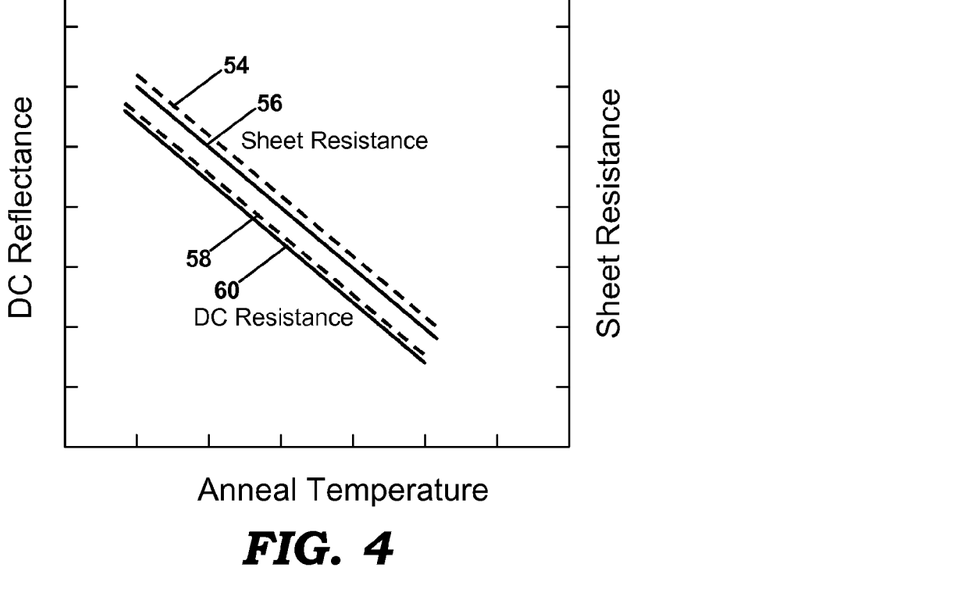
FIG. 4 depicts plots of DC reflectance and sheet resistance versus anneal temperature for two anneal times according to an embodiment of the present invention.

FIG. 4 shows an example of correlation between DC reflectances obtained from a group of substrates 16 that are annealed at different temperatures, and the sheet resistance ($R_s$) values that are measured on the same substrates 16. Lines 54 and 56 indicate sheet resistance for anneal times T2 and T1, respectively, and lines 58 and 60 indicate DC reflectance for anneal times T2 and T1, respectively. Similar to DC reflectance, sheet resistance is sensitive only to carrier activation and less sensitive to end-of-range damage in the junction. Therefore, DC reflectance can be calibrated using sheet resistance values to represent carrier activation.

For example, a set of special reference substrates 16 with known carrier activation are prepared by ion implantation and spike anneal, followed by resistivity measurements to establish the carrier activation level in each reference substrate. DC reflectance is measured on the reference substrates 16 and the correlation between the DC reflectances and the carrier activation levels is stored in the look-up table 70. DC reflectance is measured on a test substrate 16, and the carrier activation of the test substrate 16 is determined using the look-up table 70.

As depicted in FIG. 1, various embodiments of the present invention include a software module 66 which, when executed by the processor 28, determines carrier activation based on measured DC reflectance values and carrier activation values of reference substrates 16 stored in the look-up table 70.

Figure 3:
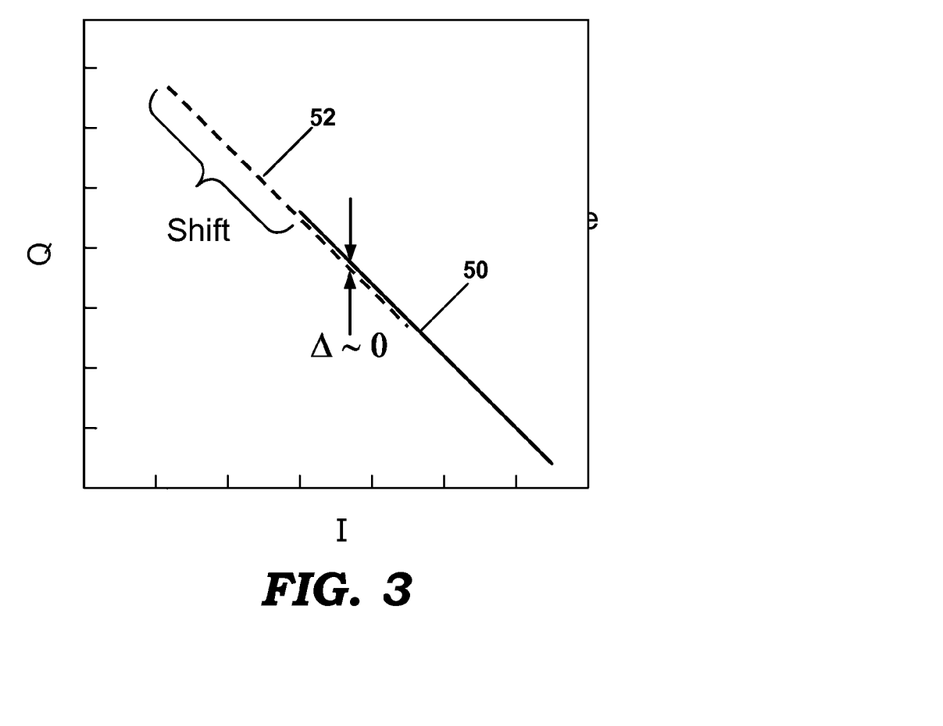
FIG. 3 depicts a plot of quadrature signals versus in-phase signals for two anneal times according to an embodiment of the present invention.

Another method for the characterization of carrier activation and end-of-range damage density is related to the analysis of the in-phase and quadrature components of the modulated optical reflectance signal. As shown in FIG. 3, the points corresponding to modulated optical reflectance signal measurements of substrates 16 treated with different anneal temperatures but the same anneal time (T2) form a straight line 50 in in-phase and quadrature signal coordinates. A line 52 corresponding to the same anneal temperatures but different anneal times (T1<T2) is shifted with respect to the line 50. Similar to the case of modulated optical reflectance signal amplitudes, the extent of this shift is indicative of the end-of-range damage density in the junction. Therefore, the system 10 can also evaluate end-of-range damage density using in-phase and quadrature signal processing.

Correlation between end-of-range damage density and the in-phase and quadrature components of the modulated optical reflectance signals may be established using the same set of reference substrates 16 as described above, which have known carrier activation and end-of-range damage levels. The in-phase and quadrature components of the thermal wave signals from these reference substrates can be measured and plotted in the in-phase and quadrature coordinates. Correlation between the shift in the in-phase and quadrature coordinates of two or more of the modulated optical reflectance data sets and the end-of-range damage density for a given carrier activation is stored in the look-up table 70. The in-phase and quadrature components of the modulated optical reflectance signal are then measured on a test substrate and analyzed in the in-phase and quadrature coordinates. The resulting shift between the position of the in-phase and quadrature point with respect to the reference value is determined and converted to end-of-range damage density using the look-up table 70.

As depicted in FIG. 1, some embodiments of the invention include a software module 64 which, when executed by the processor 28, determines end-of-range damage density based on the extent of the shift of the in-phase and quadrature signal with respect to the reference values stored in the look-up table 70.

Figure 5A:
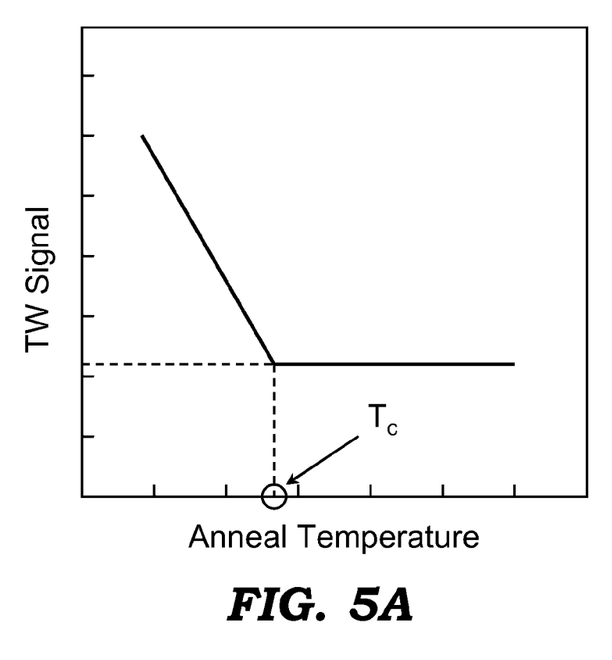
FIG. 5A depicts a plot of modulated optical reflectance signal amplitude versus anneal temperature according to an embodiment of the present invention.
Figure 5B:
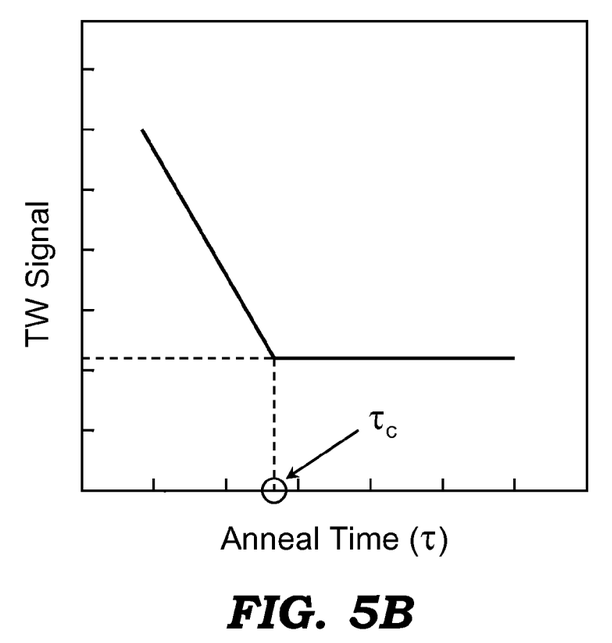
FIG. 5B depicts a plot of modulated optical reflectance signal amplitude versus anneal time according to an embodiment of the present invention.

Increasing at least one of the anneal temperature and the anneal time increases the thermal budget of the anneal process and, therefore, increases the probability of removal of most end-of-range damage in the junction. As shown in FIGS. 5A and 5B, these relatively linear relationships continue until certain critical values in anneal temperature ($T_c$) or anneal time ($\tau_c$) are reached. Increasing at least one of anneal temperature beyond $T_c$ and anneal time beyond $\tau_c$ does not result in further decrease in end-of-range damage density, since almost all of the damage has already been annealed. Correspondingly, the modulated optical reflectance signal dependencies are saturated past critical values in both anneal temperature and anneal time.

Figure 6:
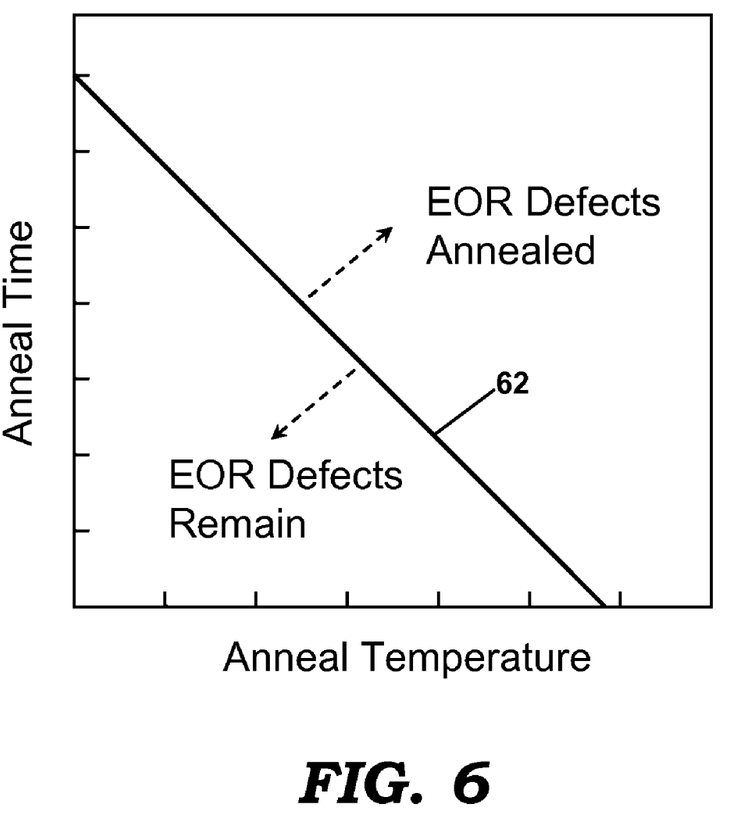
FIG. 6 depicts a phase plot indicating ranges of anneal time versus anneal temperature that are sufficient for removal of end-of-range damage according to an embodiment of the present invention.

If thermal wave measurements are performed on a series of substrates 16 at different anneal temperatures and anneal times, it is possible to represent removal of end-of-range damage in a special diagram (referred to as a phase diagram), an example of which is shown schematically in FIG. 6. In this plot, a threshold curve 62 is drawn corresponding to critical values of anneal temperature and anneal time. Above the curve 62, the anneal conditions (temperature and time) are such that substantially all end-of-range damage is removed. Correspondingly, the area below the curve 62 represents the area where the combination of anneal temperature and time is not sufficient to remove substantially all the end-of-range damage. The information provided in the diagram of FIG. 6 is valuable since it can be used to optimize the anneal process in integrated circuit processing. Although the threshold curve depicted in FIG. 6 is a straight line, it is appreciated that the present invention is not limited to relationships where the curve is a straight line. The phase diagram is generated by the off-system software, most likely a spreadsheet data analysis package, such as Microsoft Excel, for example.

In the embodiments of the present invention as described above, modulated optical reflectance amplitude is used to measure end-of-range damage density and carrier activation. In alternate embodiments, modulated optical reflectance phase is also used for this purpose. Additionally, a combination of pump DC reflectances and probe DC reflectances is used to measure carrier activation.

The foregoing descriptions of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for determining characteristics of a junction formed in a substrate, the method comprising:
   (a) periodically exciting a region of the substrate including the junction using a pump laser beam,
   (b) reflecting a probe laser beam from the region of the substrate being periodically excited,
   (c) measuring a modulated optical reflectance signal based on the probe laser beam reflected from the region of the substrate being periodically excited, and
   (d) comparing the modulated optical reflectance signal with reference signals to determine an end-of-range defect density in the junction formed in the substrate.

2. The method of claim 1 wherein the reference signals are modulated optical reflectance signals obtained from calibration substrates measured to determine the end-of-range defect density in junctions formed in the calibration substrates, wherein the calibration substrates are produced using various anneal temperatures and anneal times.

3. The method of claim 1 wherein the end-of-range defect density is determined based on a relationship between measured modulated optical reflectance signal level and an anneal temperature to which the substrate was exposed during an anneal process.

4. The method of claim 1 wherein:
   step (c) includes analyzing the reflected probe laser beam with a coherent demodulator to generate an in-phase component and a quadrature component of the modulated optical reflectance signal, and
   step (d) includes comparing the in-phase and quadrature components with the reference signals to determine the end-of-range defect density in the junction formed in the substrate.

5. The method of claim 4 wherein the end-of-range defect density is determined based on a relationship between the in-phase and quadrature components and an anneal time during which the substrate was exposed to an anneal temperature during an anneal process.

6. The method of claim 1 further comprising:
   (e) repeating steps (a) through (d) on substrates annealed at various anneal temperatures and various anneal times, and
   (f) generating a plot in a coordinate system of anneal temperature versus anneal time, the plot including a curve indicating a threshold, wherein data points above the threshold indicate removal of substantially all end-of-range defects and data points below the threshold indicate remaining end-of-range defects.

7. A method for determining characteristics of a junction formed in a substrate, the method comprising:
   (a) periodically exciting a region of the substrate including the junction using a pump laser beam,
   (b) reflecting a probe laser beam from the region of the substrate being periodically excited, (c) measuring a modulated optical reflectance based on the probe laser beam reflected from the region of the substrate being periodically excited, and
(d) comparing the modulated optical reflectance signal with reference signals to determine carrier activation in the junction formed in the substrate.

8. The method of claim 7 wherein the reference signals are modulated optical reflectance signals obtained from calibration substrates measured to determine carrier activation in junctions formed in the calibration substrates, wherein the calibration substrates are produced using various anneal temperatures and anneal times.

9. The method of claim 7 wherein carrier activation is determined based on a relationship between measured modulated optical reflectance signal level, anneal temperature to which the substrate was exposed during an anneal process, and anneal time during which the substrate was exposed to the anneal temperature.

10. A method for determining characteristics of a junction formed in a substrate, the method comprising:
   (a) periodically exciting a region of the substrate including the junction using a pump laser beam,
   (b) reflecting a probe laser beam from the region of the substrate being periodically excited,
   (c) measuring a DC reflectance signal based on the probe laser beam or the pump laser beam reflected from the region of the substrate being periodically excited, and
   (d) comparing the DC reflectance signal with reference signals to determine carrier activation in the junction formed in the substrate.

11. The method of claim 10 wherein the reference signals are DC reflectance signals obtained from calibration substrates measured to determine carrier activation in junctions formed in the calibration substrates, wherein the calibration substrates are produced using various anneal temperatures.

12. The method of claim 10 wherein the reference signals are sheet resistance signals obtained from calibration substrates measured to determine carrier activation in junctions formed in the calibration substrates, wherein the calibration substrates are produced using various anneal temperatures.

13. A method for determining characteristics of a junction formed in a substrate, the method comprising the steps of:
   (a) periodically exciting a region of the substrate including the junction using a pump laser beam,
   (b) reflecting a probe laser beam from the region of the substrate being periodically excited,
   (c) measuring a modulated optical reflectance signal based on the probe laser beam reflected from the region of the substrate being periodically excited and generating a first signal,
   (d) measuring direct current reflectances of the probe laser beam and the pump laser beam and generating second and third signals, and
   (d) determining an end-of-range defect density and carrier activation in the junction based at least in part on comparing the first, second, and third signals to reference signals.

14. The method of claim 13 wherein the reference signals are modulated optical reflectance and direct current reflectance signals obtained from calibration substrates produced using a variety of different anneal temperatures and anneal times.

* * * * *